(12) United States Patent
Bulliard et al.

(10) Patent No.: US 6,849,741 B2
(45) Date of Patent: Feb. 1, 2005

(54) METHOD FOR PREPARING COMPOUNDS DERIVED FROM THIAZOLIDINEDIONE, OXAZOLIDINEDIONE OR HYDANTOIN

(75) Inventors: Michel Bulliard, Angers (FR); Yvon Derrien, La Meignanne (FR); Tony Pintus, Bouchemaine (FR)

(73) Assignee: PPG-SIPSY (FR)

( * ) Notice: Subject to any disclaimer, the term of this patent is extended or adjusted under 35 U.S.C. 154(b) by 0 days.

(21) Appl. No.: 10/636,155

(22) Filed: Aug. 7, 2003

(65) Prior Publication Data

US 2004/0059121 A1 Mar. 25, 2004

Related U.S. Application Data

(63) Continuation of application No. PCT/FR02/00571, filed on Feb. 14, 2002.

(30) Foreign Application Priority Data

Feb. 14, 2001 (FR) ............................................. 01 02010
Apr. 17, 2001 (FR) ............................................. 01 05206

(51) Int. Cl.$^7$ ........................................... C07D 213/30
(52) U.S. Cl. .................... 546/340; 546/269.7; 548/183; 548/227
(58) Field of Search ................................. 548/183, 227; 546/269.7, 340

(56) References Cited

U.S. PATENT DOCUMENTS

| 5,399,632 A | | 3/1995 | Costello et al. |
| 5,585,495 A | * | 12/1996 | Huber .......................... 548/183 |
| 5,952,509 A | * | 9/1999 | Saito et al. .................. 546/340 |
| 6,100,403 A | * | 8/2000 | Saito et al. ............... 546/269.7 |

FOREIGN PATENT DOCUMENTS

| DE | 197 11 616 | | 9/1998 |
| EP | 0 257 781 | | 3/1988 |
| EP | 0 454 501 | | 9/2001 |
| JP | 2001011042 | * | 1/2001 |

OTHER PUBLICATIONS

Clark, abstract 114:164084 of Chemical Abstracts, J Med chem, vol. 34(1), 1991, 319–325.*
R. Bar et al., Tetrahedron Letters, vol. 22, No. 18, 1981, pp. 1709–1710, Great Britan XP002172538.
Chemical Abstracts, vol. 131, No. 18, Nov. 1, 1999, abstract No. 242903, Columbus, OH, US XP002172539.

* cited by examiner

*Primary Examiner*—D. Margaret Seaman
(74) *Attorney, Agent, or Firm*—Piper Rudnick LLP

(57) ABSTRACT

A method for preparing a thiazolidinedione, oxazolidinedione or hydantoin compound of formula (I) from a compound of formula (II):

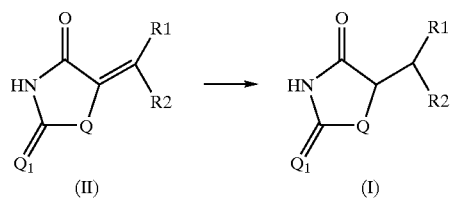

wherein Q represents an oxygen atom or a sulfur atom; Q1 represents an oxygen atom or a sulfur atom; R1 and R2, which can be identical or different, represent a hydrogen atom, a $C_{1-10}$ alkyl chain, a cycloalkyl, an alkylaryl, an arylalkyl; the alkyl, cycloalkyl, alkylaryl or arylalkyl groups being optionally substituted by an alkyl, an alkoxy or aryloxy, a halogen, a hydroxy, a sulfino, a sulfonyl, an amino such as $NH_2$, $NHR_3$, $N(R_3)_2$, wherein R3 represents an alkyl, an alkoxy or an alkylcarbonyl, reacting a compound of formula (II) with formic acid, either as a hydrogen donor in a hydrogen-transfer reaction or as a solvent in a hydrogenation reaction, in the presence of a catalyst containing a transition metal to obtain a corresponding compound of formula (I).

22 Claims, No Drawings

METHOD FOR PREPARING COMPOUNDS DERIVED FROM THIAZOLIDINEDIONE, OXAZOLIDINEDIONE OR HYDANTOIN

RELATED APPLICATION

This is a continuation of International Application No. PCT/FR02/00571, with an international filing date of Feb. 14, 2002, which is based on French Patent Application Nos. 01/02010, filed Feb. 14, 2001, and 01/05206, filed Apr. 17, 2001.

FIELD OF THE INVENTION

This invention relates to a new method for preparing thiazolidinedione, oxazolidinedione and hydantoin derivative compounds of formula (I) from compounds of formula (II) below:

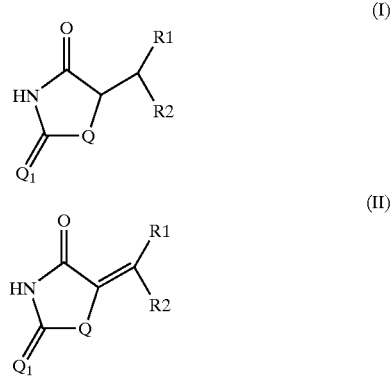

wherein:

Q is an oxygen atom or a sulfur atom;

Q1 is an oxygen atom or a sulfur atom; and

R1 and R2, which can be identical or different, represent a hydrogen atom, a $C_{1-10}$ alkyl chain, a cycloalkyl, an alkylaryl, an arylalkyl; the alkyl, cycloalkyl, alkylaryl or arylalkyl groups being optionally substituted by an alkyl, an alkoxy or aryloxy, a halogen, a hydroxy, a sulfino, a sulfonyl, an amino such as $NH_2$, $NHR_3$, $N(R_3)_2$, wherein R3 represents an alkyl, an alkoxy or an alkylcarbonyl.

BACKGROUND

The thiazolidinedione, oxazolidinedione and hydantoin derivative compounds of formula (I) are known as "synthesis intermediaries" for preparing active pharmaceutical principles or as active pharmaceutical agents such as, for example, pioglitazone, rosiglitazone, troglitazone and ciglitazone.

Known in the prior art are methods for preparing thiazolidinedione, oxazolidinedione, and hydantoin derivative compounds:

via reduction in the presence of a metal hydride as described in WO 98/37073, or via reduction in the presence of a transition metal as described in EP 257781, or via reduction in the presence of magnesium and methanol as described in WO 98/37073.

These various methods have the disadvantages of generating large amounts of impurities, which can exceed 10% in the synthesis of pioglitazone, of using a large amount of catalyst or solvent, and of having a selectivity problem in the isolation of the resultant compound of formula (I).

SUMMARY OF THE INVENTION

This invention relates to a method for preparing a thiazolidinedione, oxazolidinedione or hydantoin compound of formula (I) from a compound of formula (II):

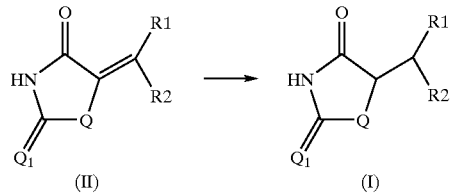

wherein Q represents an oxygen atom or a sulfur atom; Q1 represents an oxygen atom or a sulfur atom; R1 and R2, which can be identical or different, represent a hydrogen atom, a $C_{1-10}$ alkyl chain, a cycloalkyl, an alkylaryl, an arylalkyl; the alkyl, cycloalkyl, alkylaryl or arylalkyl groups being optionally substituted by an alkyl, an alkoxy or aryloxy, a halogen, a hydroxy, a sulfino, a sulfonyl, an amino such as $NH_2$, $NHR_3$, $N(R_3)_2$, wherein R3 represents an alkyl, an alkoxy or an alkylcarbonyl, reacting a compound of formula (II) with formic acid, either as a hydrogen donor in a hydrogen-transfer reaction or as a solvent in a hydrogenation reaction, in the presence of a catalyst containing a transition metal to obtain a corresponding compound of formula (I).

DETAILED DESCRIPTION

The method according to the invention has the advantages of preparing compounds of formula (I) while generating low amounts of impurities, obtaining a total transformation rate, eliminating the use of large amounts of solvent, being selective and easily isolating the product of formula (I). The method according to this invention, thus, makes it possible to reduce the economic costs of industrial production of compounds of formula (I).

In one aspect, the invention, thus, includes a method for preparing a thiazolidinedione, oxazolidinedione or hydantoin derivative compound of formula (I) from a compound of formula (II) below:

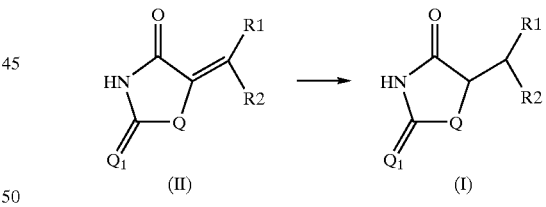

wherein Q, Q1, R1 and R2 have the same meanings as above, wherein a compound of formula (II) is reacted with formic acid, either as a hydrogen donor in a hydrogen-transfer reaction or as a solvent in a hydrogenation reaction, in the presence of a catalyst based on a transition metal to obtain the corresponding compound of formula (I).

The formic acid used can be formic acid at 100% or a solution containing formic acid with a formic acid level that can range from about 0.1 to about 99% as long as the solution can dissolve the compound of formula (II). The solution can be an aqueous solution or an organic solution or a mixture of these two.

The transition-metal based catalyst employed either in the hydrogen-transfer reaction or in the hydrogenation reaction is advantageously selected from a homogeneous or heterogeneous catalyst.

The following can be cited as homogeneous catalysts based on a transition metal: Ir(COD)Cl, Ru(p-cymene)Cl$_2$, Ru(COD)Cl$_2$, Ru(PPh$_3$)$_3$Cl$_2$, RuCl$_3$, Ru(PPH$_3$)$_4$Cl, RuCl$_3$.3H$_2$O, Ru(PPh$_3$)$_4$H$_2$, Rh(PPh$_3$)$_3$Cl, RhCl$_3$.3H$_2$O, Ru(PPh$_3$)$_4$H, Rh(COD)trifluoromethane sulfonate, (C$_6$H$_{12}$)$_3$ P(COD)pyridine-Ir(F)$_6$, Ir(PPh$_3$)$_3$H$_2$Cl, Ir(PPh$_3$)$_3$HCl$_2$, Ir(PPh$_3$)$_2$H$_3$, Ir(PPh$_3$)$_3$H$_5$, Ir(PPh$_3$)$_2$(CO)X[X=Cl, Br, I], Ir(PPh$_3$)$_2$(CO)H, Os(PPh$_3$)$_3$HCl, Pd(OAc)$_2$, PdCl$_2$, Pd(PPh$_3$)$_2$Cl$_2$, Pd(NH$_4$)$_2$Cl$_4$, Pt(PPh$_3$)$_2$Cl$_2$, PtCl$_4$K$_2$, Fe(PPh$_3$)$_2$Cl$_2$, Ni(PBu-n$_3$)$_2$, ReCl$_5$.

The following can be cited as optionally supported heterogeneous catalysts based on a transition metal: Pt, Pt/C, Pt(O)$_2$, Pd, Pd/C, Pd/CaCO$_3$, Pd/SiO$_2$, Pd/BaCO$_3$, Pd(OH)$_2$/C, Ir, Ir/C, Ru, Ru/C, Rh, Raney Ni, Fe.

The method according to the invention can optionally be implemented in the presence of a secondary solvent. Such a secondary solvent is advantageously selected from among water, a hydrocarbon such as hexane, heptane, octane, nonane, decane, benzene, toluene or xylene, an ether such as tetrahydrofuran, dioxane, dimethoxyethane, diisopropyl ether or diethylene glycol dimethyl ether, an ester such as ethyl acetate, butyl acetate or ethyl propionate, a ketone such as acetone, diisopropyl ketone, methyl isobutyl ketone, methylethyl ketone or acetylacetone, an alcohol such as methanol, ethanol, n-propanol, iso-propanol, butanol, isobutanol or methoxyethanol, an alkyl halide such as dichloromethane, chloroform or 1,2-dichloroethane, an acid such as acetic acid, propionic acid or butyric acid, an amide such as dimethylformamide or a sulfoxide such as dimethyl sulfoxide.

A preferred form of implementation of the method for the preparation of compounds of formula (I) by hydrogenation reaction according to aspects of the invention comprises the treatment of the compound of formula (II) in the presence of formic acid and a catalyst under the following conditions:
the optional presence of a secondary solvent as previously defined;
a temperature comprised between about 0 and about +150° C.;
a metal quantity/substrate quantity ratio comprised between about 1/10,000 and about 5%;
a hydrogen pressure between about 0.1 and about 50 bar;
a reaction duration comprised between about 0.5 and about 40 hours.

A preferred form of implementation of the method for preparing compounds of formula (I) by a hydrogen-transfer reaction according to the invention comprises treating the compound of formula (II) in the presence of formic acid and a catalyst under the following preferred operating conditions:
the optional presence of a secondary solvent as previously defined;
a temperature comprised between about 0 and about +150° C.;
a metal quantity/substrate quantity ratio comprised between about 1/10,000 and about 5/100;
a reaction duration comprised between about 0.5 and about 40 hours.

Other advantages and characteristics of the invention will become apparent from the examples below presented as an illustration of the method for the preparation of compounds of formula (I) from compounds of formula (II). The compounds of formula (II) constituting the substrates of the reaction can be prepared by any method of the prior art.

EXAMPLE 1
Preparation of the Compound: {[(ethyl)-5-pyridyl-2-)ethoxy-4-]benzyl}-5-thiazolidine-2,4-dione-2,4 by Means of a Hydrogenation Reaction.

The following were introduced into a Büchi device: 20 g of {[(ethyl-5-pyridyl-2-)ethoxy-4-]benzylylidene}-5-thiazolidine-2,4,-dione-2,4, 10 g of Pd/C at 10% and 200 ml of formic acid at 95-97%.

The nitrogen and then the hydrogen were purged.

The reaction medium was heated at 75-80° C. for 6 hours under a hydrogen pressure of 8 bar.

The reaction medium was cooled to ambient temperature (20-25° C.). The catalyst was filtered and rinsed with 60 ml of formic acid.

The filtrate was concentrated to 40 ml under vacuum at 40° C. We then added 80 ml of water and 60 ml of formic acid to the concentrate. The pH value of the solution was 0.93.

We then added to this medium 101 g of a solution of NaOH at 30% up to a pH value equal to 3.25. The medium was then agitated for 10 minutes at 20° C. and the product was filtered.

The crude product was washed in ethanol as follows.

The product was put into solution in 172 ml of ethanol; this was heated at reflux for 30 minutes and then cooled to 10° C. The resultant product was filtered.

After drying under vacuum at 50° C. we obtained 19.1 g of white powder.

Yield: 97.4%.

EXAMPLE 2
Preparation of the Compound: {[(ethyl-5-pyridyl-2-)ethoxy-4-]benzyl}-5-thiazolidine-2,4-dione-2,4 by Means of a Hydrogen-Transfer Reaction by Homogeneous Catalysis.

The following were introduced under nitrogen into a 50-ml flask: 1 g of {[(ethyl-5-pyri-dyl-2-)ethoxy-4-]benzylylidene}-5-thiazolidine-2,4-dione-2,4, 61 mg of chloro-1,5-COD iridium and 10 ml of formic acid at 97%.

The orangish solution was heated at reflux for 6 hours.

From the reaction medium, the HPLC profile indicated a transformation rate of 97%.

The medium was concentrated to 2 ml.

We then added 9 ml of water and filtered the product.

EXAMPLE 3
Preparation of the Compound: {[(ethyl-5-pyridyl-2-)ethoxy-4-]benzyl}-5-thiazolidine-2,4-dione-2,4 by Means of a Hydrogen-Transfer Reaction by Heterogeneous Catalysis.

The following were introduced under nitrogen into a 50-ml flask: 2.5 g of {[(ethyl-5-pyridyl-2-)ethoxy-4-]benzylylidene}-5-thiazolidine-2,4-dione-2,4, 3 g of Rh/C at 5% with a moisture level of 57.8% (2.5% of metal rhodium/substrate) and 10 ml of formic acid at 99%.

The solution was heated at reflux for 5 hours.

The HPLC profile of the reaction medium indicated a transformation rate of 78%.

The medium was concentrated to 5 ml.

We then added 9 ml of water and filtered the product.

EXAMPLE 4
Preparation of the Compound: {[(ethyl-5-pyridyl-2-)ethoxy-4-]benzyl}-5-thiazolidine-2,4-dione-2,4 by Means of a Hydrogen-Transfer Reaction by Heterogeneous Catalysis.

The following were introduced under nitrogen into a 50-ml flask: 2.5 g of {[(ethyl-5-pyridyl-2-)ethoxy-4-]benzylylidene}-5-thiazolidine-2,4-dione-2,4, 1.37 g of Pd/C at 10% with a moisture level of 53.2% (2.5% of metal palladium/substrate) and 10 ml of formic acid at 99%.

The solution was heated at reflux (105° C.) for 21 hours.

The HPLC of the reaction medium indicated a transformation rate of 66%.

The medium was concentrated to 5 ml.

We then added 19 ml of water and filtered the product.

EXAMPLE 5

Preparation of the Compound: {[(ethyl-5-pyridyl-2-)ethoxy-4-]benzyl}-5-thiazolidine-2,4-dione-2,4 by Means of a Hydrogen-Transfer Reaction by Heterogeneous Catalysis.

The following were introduced under nitrogen into a 0.5-1 flask: 20 g of {[(ethyl-5-pyri-dyl-2-)ethoxy-4-]benzylylidene}-5-thiazolidine-2,4-dione-2,4, 0.6 g of Pt(O)$_2$ (2.5% of platinum/substrate) and 200 ml of formic acid at 99%.

The solution was heated at the temperature of 84° C. for 19 hours 30 minutes.

The HPLC profile of the reaction medium indicated a transformation rate of 98.3% of product formed.

The reaction medium was filtered and the filtrate was concentrated to 40 ml.

We then added 140 ml of water and the pH was adjusted to 3.2 by addition of soda at 30%.

The product was filtered.

The product was purified by rethickening in ethanol.

After drying under vacuum at 50° C., we isolated 19.7 g of product.

Yield: 96.5%.

EXAMPLE 6

Preparation of the Compound: {[(ethyl-5-pyridyl-2-)ethoxy-4-]benzyl}-5-thiazolidine-2,4-dione-2,4 by Means of a Hydrogen-Transfer Reaction by Heterogeneous Catalysis.

The following were introduced under nitrogen into a 100-ml three-necked flask: 5 g of {[(ethyl-5-pyridyl-2-)ethoxy-4-]benzylylidene}-5-thiazolidine-2,4-dione-2,4, 0.148 g of Pt(O)$_2$ (2.5% of platinum/substrate) and 35 ml of formic acid at 99%.

The solution was heated at the temperature of 80-85° C. for 19 hours 30 minutes.

The HPLC profile of the reaction medium indicated a transformation rate of 98.4% of product formed.

The product was isolated as above with a yield of 96.5%.

EXAMPLE 7

Preparation of the Compound: {[(ethyl-5-pyridyl-2-)ethoxy-4-]benzyl}-5-thiazolidine-2,4-dione-2,4 by Means of a Hydrogen-Transfer Reaction by Heterogeneous Catalysis.

The following were introduced under nitrogen into a 100-ml three-necked flask: 5 g of {[(ethyl-5-pyridyl-2-)ethoxy-4-]benzylylidene}-5-thiazolidine-2,4-dione-2,4, 0.203 g of Pt(O)$_2$ (3.4% of platinum/substrate) and 50 ml of formic acid at 99%.

The solution was heated at the temperature of 80-85° C. for 16 hours.

The HPLC profile of the reaction mixture indicated a transformation rate of 98% of product formed.

The product was isolated as above with a yield of 94.5%.

What is claimed is:

1. A method for preparing a thiazolidinedione, oxazolidinedione or hydantoin compound of formula (I) from a compound of formula (H):

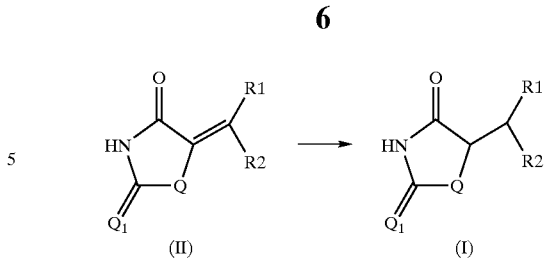

wherein:
  Q represents an oxygen atom or a sulfur atom;
  Q1 represents an oxygen atom or a sulfur atom;
  R1 and R2, which can be identical or different, represent a hydrogen atom, a $C_{1-10}$ alkyl chain, a cycloalkyl, an alkylaryl, an arylalkyl; the alkyl, cycloalkyl, alkylaryl or arylalkyl groups being optionally substituted by an alkyl, an alkoxy or aryloxy, a halogen, a hydroxy, a sulfino, a sulfonyl, an amino such as $NH_2$, $NHR_3$, $N(R_3)_2$, wherein R3 represents an alkyl, an alkoxy or an alkylcarbonyl,
  reacting a compound of formula (II) with formic acid, either as a hydrogen donor in a hydrogen-transfer reaction or as a solvent in a hydrogenation reaction, in the presence of a catalyst containing a transition metal to obtain a corresponding compound of formula (I).

2. The method according to claim 1, wherein the formic acid is formic acid at about 100% or a solution containing formic acid with a formic acid level that can range from about 0.1 to about 99%, the solution being an aqueous solution or an organic solution or a mixture thereof.

3. The method according to claim 1, wherein the transition-metal containing catalyst is a homogeneous or heterogeneous catalyst.

4. The method according to claim 3, wherein the homogeneous catalyst is selected from the group consisting of Ir(COD)Cl, Ru(p-cymene)Cl$_2$, Ru(COD)Cl$_2$, Ru(PPh$_3$)$_3$Cl$_2$, RuCl3, Ru(PPH$_4$sCl, RuCl3K$_3$H$_2$O, Ru(PPh$_3$)$_4$H$_2$, Rh(PPh$_3$)$_3$Cl, RhCl33H$_2$O, Ru(PPh$_3$)$_4$H, Rh(COD)trifluoromethane sulfonate, (C6H$_{12}$)$_3$P(COD)pyridine-Ir(F)$_6$, Ir(PPh$_3$)$_3$HzCl, Ir(PPh$_3$)$_3$HCl2, Ir(PPh$_3$)$_2$H$_3$, Ir(PPh$_3$)$_3$H$_5$, Ir(PPh$_3$)$_2$(CO)X, wherein X is Cl, Br or I, Ir(PPh$_3$h$_2$(CO)H, Os(PPh$_3$)$_3$HCl, Pd(OAc)$_2$, PdCl2, Pd(PPh$_3$)$_2$C$_2$, Pd(NH$_4$)$_2$Cl$_4$, Pt(PPh$_3$)$_2$Cl$_2$, PtCl$_1$K$_2$, Fe(PPh$_3$)$_2$Cl$_2$, Ni(PBu-n$_3$)$_2$, and ReCl$_5$.

5. The method according to claim 3, wherein the heterogeneous catalyst is selected from the group consisting of Pt, Pt/C, Pt(O)$_2$, Pd, Pd/C, Pd/CaCO$_3$, Pd/SiO$_2$, Pd/BaCO$_3$, Pd(OH)$_2$/C, Ir, Ir/C, Ru, RU/C, Rh, Raney Ni, and Fe.

6. The method according to claim 1, wherein the compound of formula (II) reacts with formic acid in the presence of a transition-metal based catalyst and in the presence of a secondary solvent.

7. The method according to claim 6, wherein the secondary solvent is selected from the group consisting of water, a hydrocarbon selected from the group consisting of hexane, heptane, octane, nonane, decane, benzene, toluene and xylene, an ether selected from the group consisting of tetrahydrofuran, dioxane, dimethoxyethane, diisopropyl ether and diethylene glycol dimethyl ether, an ester selected from the group consisting of ethyl acetate, butyl acetate and ethyl propionate, a ketone selected from the group consisting of acetone, diisopropyl ketone, methyl isobutyl ketone, methylethyl ketone and acetylacetone, an alcohol selected from the group consisting of methanol, ethanol, n-propanol, iso-propanol, butanol, isobutanol and methoxy-ethanol, an alkyl halide selected from the group consisting of dichloromethane, chloroform and 1,2-dichloroethane, an acid selected from the group consisting of acetic acid, propionic acid and butyric acid, an amide and a sulfoxide.

8. The method according to claim 1, wherein the compound of formula (II) reacts with formic acid as a solvent in a hydrogenation reaction in the presence of hydrogen, and in the presence of a transition-metal based catalyst under the following operating conditions:

the optional presence of a secondary solvent;

a temperature comprised between about 0 and about +150° C.;

a metal quantity/substrate quantity ratio comprised between about 1/10,000 and about 5%;

a hydrogen pressure between about 0.1 and about 50 bar;

a reaction duration comprised between about 0.5 and about 40 hours.

9. The method according to claim 1, wherein the compound of formula (II) reacts with formic acid as a hydrogen donor in a hydrogen-transfer reaction, in the presence of a transition-metal based catalyst under the following operating conditions:

the optional presence of a secondary solvent;

a temperature comprised between about 0 and about +150° C.;

a metal quantity/substrate quantity ratio comprised between about 1/10,000 and about 5/100;

a reaction duration comprised between about 0.5 and about 40 hours.

10. The method according to claim 1, wherein the reaction is carried out at 8 bar.

11. The method according to claim 1, wherein the reaction is carried out for 5–21 hours.

12. A method for preparing a thiazolidinedione, oxazolidinedione or hydantoin compound of formula (I) from a compound of formula (II):

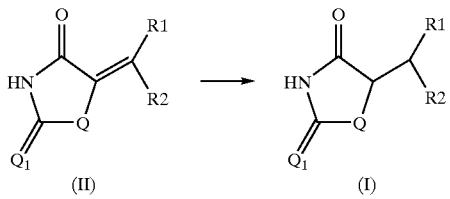

wherein:

Q represents a sulfur atom;

Q1 represents an oxygen atom;

R1 represents a hydrogen atom; and

R2 represents an alkylaryl substituted by an alkoxy, reacting a compound of formula (II) with formic acid, either as a hydrogen donor in a hydrogen-transfer reaction or as a solvent in a hydrogenation reaction, in the presence of a catalyst containing a transition metal to obtain a corresponding compound of formula (I).

13. The method according to claim 12, wherein R2 represents:

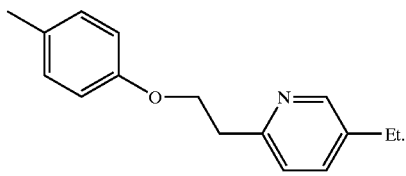

14. The method according to claim 12, wherein the formic acid is formic acid at about 100% or a solution containing formic acid with a formic acid level that can range from about 0.1 to about 99%, the solution being an aqueous solution or an organic solution or a mixture thereof.

15. The method according to claim 12, wherein the transition-metal containing catalyst is a homogeneous or heterogeneous catalyst.

16. The method according to claim 12, wherein the homogeneous catalyst is selected from the group consisting of Ir(COD)Cl, Ru(p-cymene)Cl$_2$, Ru(COD)Cl$_2$, Ru(PPh$_3$)$_3$Cl$_2$, RuCl$_3$, Ru(PPH$_3$)$_4$Cl, RuCl$_3$·3H$_2$O, Ru(PPh$_3$)$_4$H$_2$, Rh(PPh$_3$)$_3$Cl, RhCl$_3$·3H$_2$O, Ru(PPh$_3$)$_4$H, Rh(COD)trifluoromethane sulfonate, (C$_6$H$_{12}$)$_3$P(COD)pyridine-Ir(F)$_6$, Ir(PPh$_3$)$_3$H$_2$Cl, Ir(PPh$_3$)$_3$HCl$_2$, Ir(PPh$_3$)$_2$H$_3$, Ir(PPh$_3$)$_3$H$_5$, Ir(PPh$_3$)$_2$(CO)X, wherein X is Cl, Br or I, Ir(PPh$_3$)$_2$(CO)H, Os(PPh$_3$)$_3$HCl, Pd(OAc)$_2$, PdCl$_2$, Pd(PPh$_3$)$_2$Cl$_2$, Pd(NH$_4$)$_2$Cl$_4$, Pt(PPh$_3$)$_2$Cl$_2$, PtCl$_4$K$_2$, Fe(PPh$_3$)$_2$Cl$_2$, Ni(PBu-n$_3$)$_2$, and ReCl$_5$.

17. The method according to claim 12, wherein the heterogeneous catalyst is selected from the group consisting of Pt, Pt/C, Pt(O)$_2$, Pd, Pd/C, Pd/CaCO$_3$, Pd/SiO2, Pd/BaCO$_3$, Pd(OH)$_2$/C, Ir, Ir/C, Ru, Ru/C, Rh, Raney Ni, and Fe.

18. The method according to claim 12, wherein the compound of formula (II) reacts with formic acid in the presence of a transition-metal based catalyst and in the presence of a secondary solvent.

19. The method according to claim 12, wherein the secondary solvent is selected from the group consisting of water, a hydrocarbon selected from the group consisting of hexane, heptane, octane, nonane, decane, benzene, toluene and xylene, an ether selected from the group consisting of tetrahydrofuran, dioxane, dimethoxyethane, diisopropyl ether and diethylene glycol dimethyl ether, an ester selected from the group consisting of ethyl acetate, butyl acetate and ethyl propionate, a ketone selected from the group consisting of acetone, diisopropyl ketone, methyl isobutyl ketone, methylethyl ketone and acetylacetone, an alcohol selected from the group consisting of methanol, ethanol, n-propanol, iso-propanol, butanol, isobutanol and methoxy-ethanol, an alkyl halide selected from the group consisting of dichloromethane, chloroform and 1,2-dichloroethane, an acid selected from the group consisting of acetic acid, propionic acid and butyric acid, an amide and a sulfoxide.

20. The method according to claim 12, wherein the compound of formula (II) reacts with formic acid as a solvent in a hydrogenation reaction in the presence of hydrogen, and in the presence of a transition-metal based catalyst under the following operating conditions:

the optional presence of a secondary solvent;

a temperature comprised between about 0 and about +150° C.;

a metal quantity/substrate quantity ratio comprised between about 1/10,000 and about 5%;

a hydrogen pressure between about 0.1 and about 50 bar;

a reaction duration comprised between about 0.5 and about 40 hours.

21. A method for preparing {[(ethyl)-5-pyridyl-2-)ethoxy-4-]benzyl}-5-thiazolidine-2,4-dione-2,4 by means of a hydrogenation reaction from a compound of Formula II:

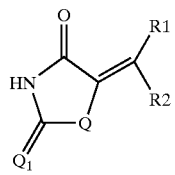
(II)

wherein:

Q represents a sulfur atom;

Q1 represents an oxygen atom;

R1 represents a hydrogen atom; and

R2 represents:

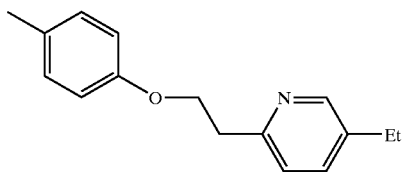

by reacting a compound of Formula II with formic acid as a hydrogen donor in a hydrogen-transfer reaction in the presence of a catalyst containing a transition metal.

22. A method for preparing {[(ethyl)-5-pyridyl-2-)ethoxy-4-]benzyl}-5-thiazolidine-2,4-dione-2,4 by means of a hydrogenation reaction from a compound of Formula II:

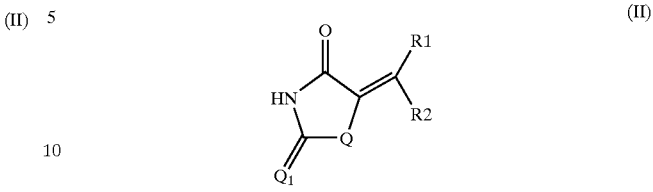
(II)

wherein:

Q represents a sulfur atom;

Q1 represents an oxygen atom;

R1 represents a hydrogen atom; and

R2 represents:

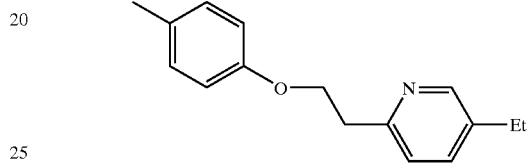

by reacting a compound of Formula II with formic acid as a solvent in a hydrogenation reaction in the presence of a catalyst containing a transition metal.

* * * * *